United States Patent [19]

Donahue et al.

[11] Patent Number: 5,767,520
[45] Date of Patent: Jun. 16, 1998

[54] RADIATION DOSIMETRY METHOD AND APPARATUS

[75] Inventors: J. Michael Donahue, Oakland, N.J.; David F. Lewis, Monroe, Conn.; Henry Seiwatz, Wayne, N.J.; Carl A. Listl, New Hyde Park, N.Y.

[73] Assignee: ISP Investments Inc., Wilmington, Del.

[21] Appl. No.: 756,010

[22] Filed: Nov. 25, 1996

Related U.S. Application Data

[63] Continuation-in-part of Ser. No. 554,540, Nov. 7, 1995, Pat. No. 5,637,876.
[51] Int. Cl.$^6$ .................................................. G01J 1/02
[52] U.S. Cl. .............................. 250/474.1; 250/475.2
[58] Field of Search ........................ 250/474.1, 475.2, 250/473.1, 472.1, 580, 484.3, 484.4, 252.1

[56] References Cited

U.S. PATENT DOCUMENTS

| | | | |
|---|---|---|---|
| 3,726,034 | 4/1973 | De Belder et al. | 250/475.2 |
| 4,059,357 | 11/1977 | Klein | 356/243 |
| 4,454,421 | 6/1984 | Tanaka et al. | 250/474.1 |
| 4,913,881 | 4/1990 | Evers | 422/56 |
| 5,637,876 | 6/1997 | Donahue et al. | 250/474.1 |

Primary Examiner—Michael J. Tokar
Assistant Examiner—Richard Hanig
Attorney, Agent, or Firm—Jules E. Goldberg; William J. Davis; Marilyn J. Maue

[57] ABSTRACT

A method for determining a level of exposure to radiation utilizes a radiation dosimeter comprising a substrate provided with a radiation sensitive layer or patch having an optical density which varies in accordance with the degree of radiation exposure. In addition, the substrate is provided with optically readable coding which identifies one or more encoded mathematical parameters for enabling an automated calculation of dosage from a detected optical density change of the radiation sensitive material. In the method, the coding on the dosimeter substrate is scanned to automatically determine the encoded mathematical parameters, and a plurality of pre-exposure optical densities and a plurality of post-exposure optical densities of the layer of radiation sensitive material in a plurality of wavelength bands are optically measured. From these quantities, a quantitative radiation dose to which the layer of radiation sensitive material was exposed is automatically computed in accordance with a predetermined mathematical algorithm. Each dosimeter is provided with a unique identification code encoded in the bar coding on the dosimeter substrate, to enable memory storage of pre-exposure optical densities for multiple dosimeters.

22 Claims, 4 Drawing Sheets 5,767,520

RADIATION DOSIMETRY METHOD AND APPARATUS

CROSS-REFERENCE TO RELATED APPLICATION

This application is a continuation-in-part of application Ser. No. 08/554,540, filed Nov. 7, 1995, now U.S. Pat. No. 5,637,876.

FIELD OF THE INVENTION

This invention relates to a radiation dosimetry method and associated devices, including a dosimeter, for carrying out the method. More particularly, this invention relates to a method and associated apparatus for quantitatively determining, in a convenient and timely manner, a dose of radiation applied to a patient or other subject.

This invention also relates to a method for manufacturing a radiation dosimeter used in the dosimetry method. More particularly, this invention relates to a manufacturing method wherein radiation sensitive patches of radiation dosimeters are individually calibrated for sensitivity to facilitate eventual use in quantitatively measuring radiation doses.

BACKGROUND OF THE INVENTION

In facilities where radioactive materials are used, for example, in hospitals where cancer patients receive radiation treatments or in blood banks where blood products are irradiated, various methods are used to quantitatively determine the radiation dose. The methods practiced include the use of thermoluminescent dosimeters (TLD's), ionization-type radiation detectors, photographic film, and radiochromic materials. TLD's are inconvenient because they require a complicated and time-consuming read-out process. Ionization-type radiation detectors are awkward and unwieldy and require a complicated setup. Photographic film requires a time-consuming chemical processing procedure before read-out. Radiochromic materials are inconvenient in current practice because the calculation of the dose requires a complex sequence of steps, subject to operator error.

SUMMARY OF THE INVENTION

An object of the present invention is to provide a new dosimetry methodology which is easy to use and less cumbersome than conventional techniques. Another object of the present invention is to provide such a methodology wherein quantitative dose information is available almost immediately after irradiation.

A further, more particular, object of the present invention, is to provide a dosimetry method wherein the user or operator does not have to calibrate the dosimetry medium or calculate the dose.

Yet another object of the present invention is to provide a dosimeter and a dose reader instrument which co-function to implement a dose determination. More particularly, it is desired to provide a dose reader which cooperates with dosimeters of different sensitivities, whereby the dose reader can be used for different applications having respectively divergent ranges of dosage.

A further object of the present invention is to provide an improved method for manufacturing radiation dosimeters utilizable in the dosimetry method disclosed herein.

A more specific object of the present invention is provide a method for manufacturing individually calibrated dosimeters utilizable in the dosimetry method disclosed herein.

The present invention is used with a radiation dosimeter in procedures for determining a level of radiation to which a patient is subjected during radiation treatment. The dosimeter comprises a substrate provided with a layer of radiation sensitive material. The radiation sensitive material has an optical density which varies systematically in accordance with the degree of radiation exposure. In addition, the substrate is provided with optically readable coding which identifies encoded mathematical parameters for enabling an automated calculation of dosage from a detected post-exposure optical density (or change in optical density) of the radiation sensitive material. As described in detail hereinafter, where the post-exposure optical density varies as a linear function of the amount of radiation exposure, the mathematical parameters include a slope parameter and, optionally, a y-intercept parameter. Of course, depending in part on the nature of the radiation sensitive material and its mode of application to the dosimeter, a different quantitative relationship such as a higher order polynomial function may describe the variation of the radiation dose in accordance with the post-exposure optical density or change in optical density of the radiation sensitive material.

The radiation sensitive material may be the radiochromic film material disclosed in U.S. Pat. Nos. 4,734,355, 4,784, 934, and 5,002,852. This film material contains a dispersion of a crystalline polyacetylenic compound as the radiation sensitive chemical. One implementation that is of utility here is a six-layer lamination of the film material. The reason for the six layers is twofold: (1) to obtain a sensitivity sufficient to enable the response to ionizing radiation doses as low as 20 cGy, and (2) to permit a film construction that presents film base to the outside world on both sides (the lamination is coating side to coating side).

The dosimeter may take the form of a card or a flexible substrate which is positionable on the patient or other irradiation subject and which is also positionable in, or slidable through a slot in, a dose reader, described below. Preferably, the coding on the substrate takes the form of a bar code. In that case, the coding and the optical density of the exposed layer of radiation sensitive material may be read by the same dose reader instrument. The bar coding and the intensity of light emanating from the radiation sensitive layer may be sensed during a sliding of the dosimeter through a slot on the dose reader instrument. Alternatively, movable optical elements may be provided for reading the bar code information and measuring the optical density of the radiation sensitive layer while the dosimeter is held in a slot or recess on the dose reader instrument.

A dose reader instrument for use with the dosimeter in measuring a radiation level to which a patient or other object is subjected comprises, in accordance with the present invention, an optical detector assembly for making a succession of measurements of light intensity in a plurality of different wavelength bands. The optical detector assembly includes a light source for generating light at a plurality of different frequencies successively. The optical detector assembly further includes an optical sensor for sensing a range of intensities of light emanating from a substrate of radiation sensitive material in response to light from the light source. The dose reader instrument also comprises a measuring device operatively connected to the optical sensor for determining an optical density of a layer of radiation sensitive material on the substrate. A decoder is operatively connected to the optical sensor for decoding mathematical parameters encoded in an optically readable coding on the substrate. A computer or microprocessor is operatively connected to the measuring device and the decoder for computing, according to a predetermined mathematical function including a measured post-exposure value of the optical density and parameters determined from the coding by the decoder, a quantitative radiation dose to which the layer of radiation sensitive material was exposed. A communicating component is operatively connected to the computer or microprocessor for communicating the computed quantitative radiation dose to an operator.

The dose reader may include a frame and a holder such as a slot or recess provided on the frame for at least temporarily positioning the substrate at a pre-established distance from to the optical sensor during measurement of the optical density of the radiation sensitive layer on the substrate, while the optical sensor may include a light source and a photocell fixed to the frame. Preferably, the optical detector assembly comprises a spectrophotometer for measuring plural optical densities of the layer of radiation sensitive material at different wavelength bands.

According to another feature of the present invention, the dose reader further comprises a timer operatively coupled to the computer for enabling the computation of the quantitative radiation dose only upon the lapse of a preset interval after exposure of the layer of radiation sensitive material to radiation. Alternatively, the timer may measure the time interval between the exposure of the radiation sensitive material to radiation and the measurement of the post-exposure optical densities of the radiation sensitive layer on the dosimeter. In that event, the difference between the measured interval and a preset time period determines a modification amount or adjustment factor to be applied to a calculated radiation dose to derive a final computed radiation dose.

As discussed above with respect to the structure of the dosimeter, where the radiation level to which a subject is exposed is linearly related to the change in the optical density of the exposed layer of radiation sensitive material, the mathematical parameters encoded on the dosimeter include a slope parameter and, optionally, a y-intercept parameter. The predetermined mathematical function used in computing the level of radiation exposure is $[\log[I(0)-D]-\log[I(s)-D]-b]/m$ where D is a premeasured background intensity determined for the instrument during production and assembly, m is the slope parameter, b is the y-intercept parameter, I(0) is a sensed pre-exposure intensity of light emanating from the layer of radiation sensitive material in response to light from a source, I(s) is a sensed post-exposure intensity of light emanating from the layer of radiation sensitive material in response to light from the source, $\log[I(0)-D]$ is proportional to a pre-exposure optical density of the layer of radiation sensitive material, $\log[I(s)-D]$ is proportional to a post-exposure optical density of the layer of radiation sensitive material, and $[\log[I(0)-D]-\log[I(s)-D]]$ is a measured optical density change in the layer of radiation sensitive material.

Where another mathematical function describes the relationship between post-exposure optical density of a radiation sensitive dosimeter layer and the degree of irradiation, different mathematical parameters are encoded on the dosimeter, e.g., in a bar code. The principle underlying the invention is that the calibration information pertaining to the relationship between an optical density change of a radiation sensitive dosimeter layer and the degree of irradiation is encoded on the dosimeter itself, thereby enabling automatic computation of the radiation dosage from a measured optical density change.

A method for determining a level of exposure to radiation utilizes the radiation dosimeter described above. The method comprises, in accordance with the present invention, optically measuring a plurality of first optical densities of the layer of radiation sensitive material at respective different wavelength bands prior to exposure of the radiation sensitive material to radiation, and optically scanning the coding to automatically determine the mathematical parameters. The layer of radiation sensitive material is exposed to radiation after the measurement of the first optical densities. Then, a plurality of second optical densities of the layer of radiation sensitive material is measured. The method also comprises automatically computing, from the first optical densities, the second optical densities, and the mathematical parameters and in accordance with a predetermined mathematical algorithm, a quantitative radiation dose to which the layer of radiation sensitive material was exposed. The automatic computing of the quantitative radiation dose includes summing the first optical densities to provide a first optical density area measurement and summing the second optical densities to provide a second optical density area measurement, the quantitative radiation dose being automatically computed from the first optical density area measurement, the second optical density area measurement and the mathematical parameters and in accordance with the predetermined mathematical algorithm.

The scanning of the coding to determine the mathematical parameters is performed prior to exposure of the layer of radiation sensitive material to radiation. However, the scanning of the parametric coding and the determination of the mathematical parameters may be implemented later, for example, at the time the post-exposure optical densities of the radiation sensitive material is undertaken.

An optical density of the layer of radiation sensitive material may be measured by sensing a reflection or transmission intensity of the layer. The optical density to be measured is related logarithmically to the sensed reflection or transmission intensity. To sense the intensity, a reflection densitometer may be used or, preferably, a spectrophotometer, as discussed above.

The optical measuring of a selected optical density includes using the spectrophotometer to measure a first intensity $J_{lamp}$ of light emitted from a source in one of the different wavelength bands and further using the spectrophotometer to measure a second intensity $J_{dosimeter}$ of light transmitted through the layer of radiation sensitive material from the source in the one wavelength band, the optical measuring of the selected optical density further including calculating the selected optical density pursuant to the relation $\log[J_{lamp}/J_{dosimeter}]$.

It is within the contemplation of the present invention that a single subject may be provided with more than one dosimeter prior to an irradiation procedure. In that event, it is advantageous if the substrates of the dosimeters are provided with additional optically readable coding identifying the respective dosimeters and enabling association of measured pre-exposure optical densities (or reflection/transmission intensities) with the proper dosimeters for computing respective quantitative radiation doses. Generally, the measured pre-exposure densities (or reflection/transmission intensities) are automatically stored by the dose reader instrument in association with the read dosimeter identities. For example, memory locations for the measured pre-exposure densities (or reflection/transmission intensities) may be determined by the dosimeter identities. Alternatively, both the measured pre-exposure densities and the respective dosimeter identities may be stored at associated locations. Upon reading a dosimeter identity from a substrate coding during a post-exposure optical density measurement, the computer or microprocessor scans the memory for the previously measured pre-exposure optical density (or reflection/transmission intensity) for that dosimeter. Then the pre-exposure optical density and the post-exposure optical density for the same dosimeter are used in calculating the radiation dose experienced by that dosimeter.

After the determination of the pre-exposure optical densities of the radiation sensitive layer, the substrate is removed from the dose reader instrument and then placed on a subject, prior to the exposure of the radiation sensitive material to radiation. After exposure and prior to optical scanning of the layer to determine the post-exposure optical densities, the substrate is temporarily placed again at the pre-established location on, or slot in, the dose reader instrument. In accordance with the present invention, where the predetermined mathematical function is linear, the radiation dose is computed according to the function [log[I(0)−D]−log[I(s)−D]−b]/m, discussed above. This linear function pertains when the post-exposure measurement is performed a known or predetermined interval after the irradiation. If the measurement takes place at a different time after exposure of the dosimeter, the same function may be used to compute a dose value which is then modified automatically by an amount determined by the difference between the preset interval and the actual post-exposure time that the measurement is made. The modification amount or factor may be taken from a table of experimentally predetermined values stored, for example, in a computer memory.

A method for determining a level of exposure to radiation, in accordance with a broader conceptualization of the present invention, utilizes a radiation dosimeter including a layer of radiation sensitive material on a substrate, the radiation sensitive material having an optical density which varies in accordance with a degree of radiation exposure. The method includes (I) scanning the substrate to determine calibration information relating to the layer of radiation sensitive material, (II) optically measuring the pre-exposure optical density of the radiation sensitive layer, (III) exposing the layer of radiation sensitive material to radiation, (IV) optically measuring the post-exposure optical density of the radiation sensitive layer, and (V) automatically computing, from the calibration information, the pre-exposure optical density and the post-exposure optical density and in accordance with a predetermined mathematical algorithm, a quantitative radiation dose to which the radiation sensitive layer was exposed.

Where the radiation dosimeter also includes an optically readable coding which identifies encoded mathematical parameters for use in computing the radiation dose, the scanning of the substrate includes a reading of the mathematical parameters from the coding. The mathematical parameters are, for example, constants in an experimentally determined functional relationship used in deriving a quantitative value for the amount of radiation exposure. As discussed above, the predetermined functional relationship may be the linear function [log[I(0)−D]−log[I(s)−D]−b]/m where D is a premeasured background intensity, m is a slope parameter included in the mathematical parameters, b is a y-intercept parameter included in the mathematical parameters, I(0) is a sensed pre-exposure reflection or transmission intensity of the layer of radiation sensitive material, I(s) is a sensed post-exposure reflection or transmission intensity, log[I(0)−D] is proportional to a pre-exposure optical density of the layer of radiation sensitive material, log[I(s)−D] is proportional to a post-exposure optical density of the layer of radiation sensitive material, and [log[I(0)−D]−log[I(s)−D]] is a measured optical density change in the layer of radiation sensitive material.

Preferably, the optical measuring of the post-exposure optical densities of the radiation-sensitive material is performed only after a pre-determined interval has elapsed after exposure of the layer to radiation. However, if circumstances require measurement of the post-exposure optical densities at a different time, the difference between the actual measurement time and the preferred time may be used to determine a modification amount or factor, e.g., selected from a table of experimentally predetermined values, for adjusting the result of the above-described computation. Such circumstances might occur, for example, where the use of several dosimeters on the irradiation subject necessarily results in at least one post-exposure optical measurement made before or after the preset interval has expired (assuming the use of the same dose reader).

A radiation dose determination method in accordance with the present invention is easier to use than conventional methods and provides a virtually real time determination of radiation dosage. The ease of use and the practicable immediacy of results are enabled in part by the previously implemented calibration of the dosimetry medium, i.e., the radiation sensitive layer on the dosimeter, at the time of the radiation. In contrast to other radiation level determination procedures, such as those dosage measurements using other radiochromic materials, the user does not have to expend effort in calibrating the dosimetry medium. Furthermore, the present technique is much quicker and easier to use than thermoluminescent dosimeters, which require extensive effort and time to read out the results.

In practice, each manufactured batch of radiation sensitive material characterized by a linear mathematical function may be tested to determine the slope and intercept parameters which define the linear optical sensitivity of the radiation sensitive material. The slope parameter and, optionally, the intercept parameter are encoded on each dosimeter for use by the computer or microprocessor of the dose reader instrument in calculating a dose level from the change in the optical density of the radiation sensitive layer on the particular dosimeter. Several different types of dosimeters may be provided, having respective sensitivities, and thus respective calibration parameters, for use in different applications.

The incorporation of calibration information into the dosimeters enables the use of a standardized dose reader instrument, regardless of the application.

A dosimeter of the above-described type, and particularly the layer of radiation sensitive material thereof, is a kind of sensor which has an irreversible reaction when subjected to an action such as high-energy ionizing electromagnetic energy (X-rays, gamma rays). The reaction is progressive, i.e., varies with the amount of the action to which the sensor is subjected. In addition, the reaction is cumulative, i.e., exhibits a total reaction which is a function of the sum of all the actions to which the sensor is subjected. Moreover, it is to be recognized that the dosimeters of the above-described type are not necessarily disabled from reacting to further action after being subjected to one or more initial actions. In dosimeters used in the dose-measuring method discussed above, a general mathematical function which describes the relationship between the action and the reaction is known. The calibration process serves to determine specific constants of the mathematical function.

Pursuant to the above observations, the present invention also provides a method for manufacturing calibrated sensors of the type which have an irreversible reaction when subjected to an action (e.g., energy), wherein the reaction is progressive and cumulative and related by a known generic mathematical function to the action.

The above-described dosimetry techniques may be used with dosimeters which are calibrated by lot. However, it is possible to individually calibrate dosimeters and to provide the measured and calculated parameters on the respective dosimeters.

In a method for manufacturing an individually calibrated dosimeter in accordance with the present invention, a layer of radiation sensitive material is applied to a substrate, the radiation sensitive material having an optical density which varies in accordance with a degree of radiation exposure. A plurality of pre-exposure optical densities of the layer of radiation sensitive material is optically measured and subsequently the layer of radiation sensitive material is exposed to a known dose of radiation. Thereafter, a plurality of post-exposure optical densities of the layer of radiation sensitive material is optically measured. Using at least the pre-exposure optical densities, the post-exposure optical densities, and the known dose of radiation, one computes mathematical parameters defining a predetermined mathematical function. The computed mathematical parameters are applied in encoded form to the substrate (e.g., printed in bar code form on the substrate or a holder card).

In accordance with a preferred embodiment of the present invention, many, if not all, of the steps in the manufacturing process are performed automatically. Specifically, the optical measuring of the pre- and post-exposure optical densities of the layer of radiation sensitive material and the computing of the calibration parameters are performed automatically. In addition, the computed mathematical parameters may be reduced automatically to encoded form and applied automatically to (e.g., printed on) the substrate. Also, the pre-exposure optical densities are automatically stored in electronically encoded form and subsequently automatically retrieved to compute the mathematical parameters.

Preferably, the mathematical parameters are encoded in optically readable form such as in bar codes.

In accordance with another feature of the present invention, the manufacturing method further comprises the step of automatically generating an identification code for the substrate, to distinguish the substrate from other substantially similar substrates under manufacture. The identification code facilitates or enables a computerized, assembly-line manufacturing operation by enabling the association of the proper pre-exposure and post-exposure optical densities.

As described above with respect to the dosimetry method of the present invention, the pre-exposure optical densities and the post-exposure optical densities of any selected layer of radiation sensitive material may be measured by operating a spectrophotometer apparatus, so that the different pre-exposure optical densities, as well as the post-exposure optical densities, are determined from transmission or reflection intensities at respective different wavelength or frequency bands. The pre-exposure optical densities are added to form a first optical density area measurement, while the post-exposure optical densities are added to form a second optical density area measurement. The two optical density area measurements are used in the mathematical function to compute the calibration parameters for the individual dosimeter.

The substrate is preferably provided with optically readable coding uniquely identifying the respective dosimeter.

As discussed above, the mathematical function may be a linear function, so that the calibration parameters include a slope parameter and, optionally, a y-intercept parameter. According to a more specific feature of the present invention, measuring the pre-exposure optical densities includes the step of sensing pre-exposure reflection or transmission intensities of the layer of radiation sensitive material, the step of measuring the post-exposure optical densities including the sensing post-exposure reflection or transmission intensities of the layer of radiation sensitive material. The predetermined mathematical function is $E_r = [\log[I(0)-D]-\log[I(s)-D]-b]/m$ where $E_r$ is the known radiation dose, D is a premeasured background intensity, m is a slope parameter included in the mathematical parameters, b is a y-intercept parameter included in the mathematical parameters, I(0) is the sensed pre-exposure reflection or transmission intensity, and I(s) is the sensed post-exposure reflection or transmission intensity.

A manufacturing method in accordance with the present invention produces radiation dosimeters used to make dose measurements whose accuracy depends only on the accuracy of the calibration and not on the uniformity of the radiation sensitive material in a manufacturing lot or batch. Accordingly, dosimetry errors are eliminated which would normally be caused by variations in the radiation sensitivity of individual patches because of manufacturing tolerances.

In a dosimeter manufacturing method in accordance with the present invention, production quality standards may be relaxed without affecting system performance. This results in less waste and lower costs. A dosimeter manufacturing method in accordance with the present invention provides the potential for producing high-accuracy dosimeters routinely at low cost.

BRIEF DESCRIPTION OF THE DRAWINGS

FIG. 6 is the same as FIG. 2, identical reference designations have been used.

DETAILED DESCRIPTION

Figure 1:
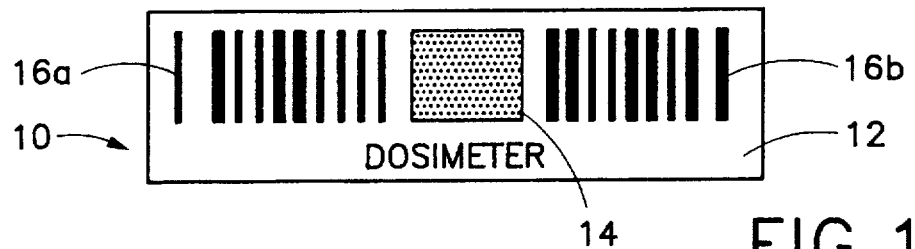
FIG. 1 is a plan view of a dosimeter or radiation measurement patch manufactured in accordance with the present invention.

As illustrated in FIG. 1, a radiation dosimeter 10 comprises a planar substrate or carrier 12 which can be positioned on a patient or other person or object to which radiation is applied. Dosimeter 10 is used, as discussed in detail hereinafter, for determining a level of radiation to which a patient, person or object is subjected during a radiation treatment procedure. Substrate 12 is provided with a patch or layer 14 of radiation sensitive material. The radiation sensitive material has an optical density which varies systematically, e.g., linearly, in accordance with the amount of radiation exposure. In addition, substrate 12 is provided with one or more optically readable bar codes 16a, 16b which identify encoded mathematical parameters, particularly a slope and an intercept of a linear equation or expression. These encoded mathematical parameters enable an automated calibration of the sensitivity of the particular radiation sensitive patch or layer 14 of dosimeter 10 and concomitantly enable an automated calculation of radiation dosage from a detected change in optical density of the radiation sensitive material of patch 14.

Although FIG. 1 shows two bar codes 16a and 16b, it may be preferable, for example, for space reasons, to provide a single bar code, i.e., a single series of bars of varying widths. Moreover, the bar coding 16a, 16b on substrate 12 may include a unique identification of the respective dosimeter, enabling a seriatim measurement of several pre-exposure optical densities and storage of the measured densities in memory for later selective recall. This option is particularly useful where several dosimeters 10 are applied to the same subject and exposed during the same irradiation process.

Figure 2:
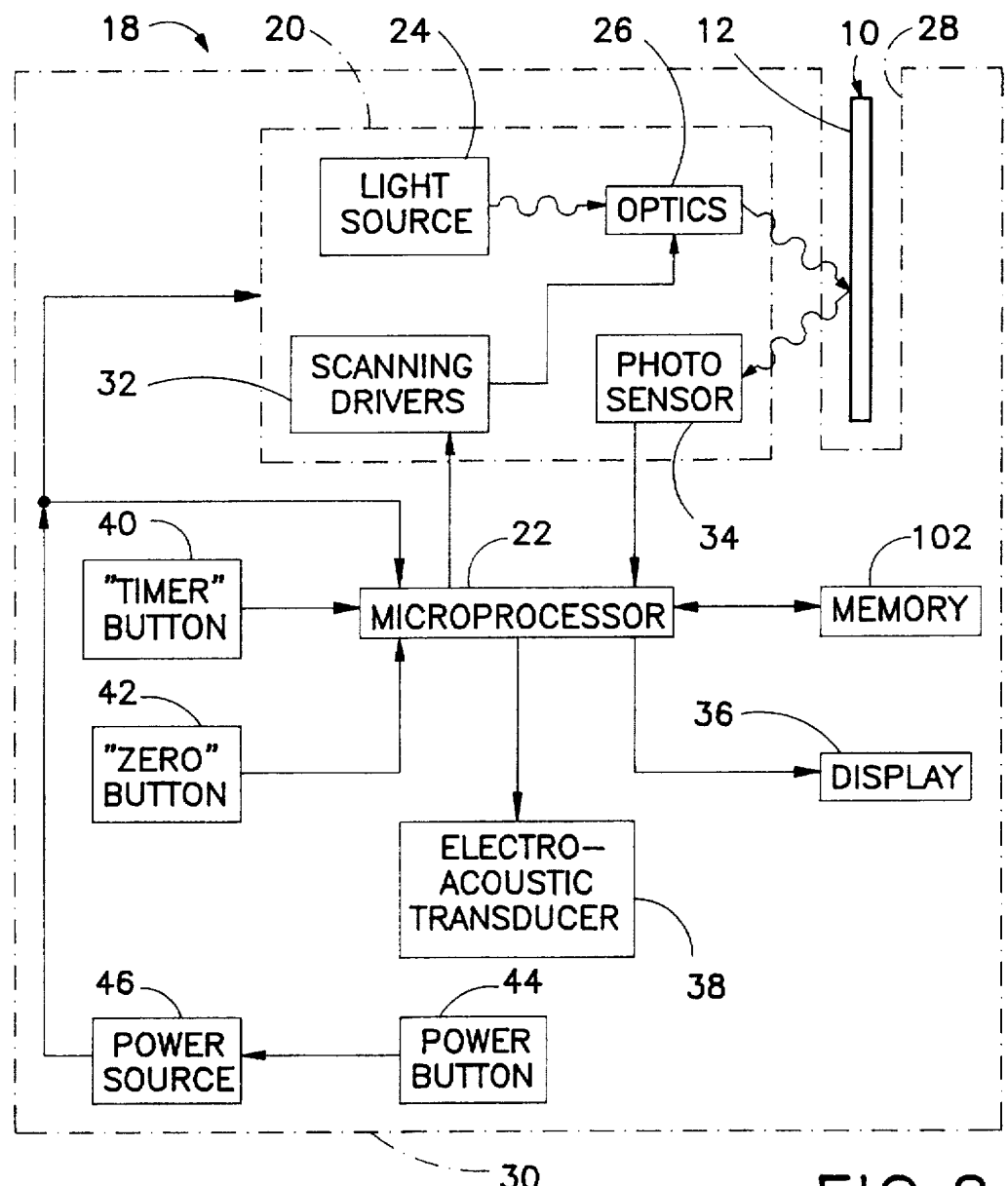
FIG. 2 is a block diagram of a dose reader used to determine a radiation dosage received by the dosimeter of FIG. 1.

Prior to and after exposure of patch 14 to radiation, the optical density of the radiation sensitive material of the patch is measured by a dose reader 18, illustrated diagrammatically in FIG. 2. Dose reader 18 comprises an optical scanner or reflection densitometer 20 for sensing a range of variable reflection intensities at a multiplicity of different locations on substrate 12. The optical scanner or scanning reflection densitometer 20 cofunctions with a microprocessor 22 to determine or measure an optical density of radiation sensitive patch 14 and to decode the mathematical parameters encoded in bar codes 16a and 16b. A measured optical density is logarithmically related to a sensed reflection intensity, as indicated in greater detail hereinafter.

Optical scanner or scanning reflection densitometer 20 includes a light source 24 which produces electromagnetic radiation of a predetermined intensity and range of wavelengths. The electromagnetic radiation from light source 24 is directed by optical elements 26 to dosimeter 10, which is held in a slot 28 in a frame or casing 30. Optical elements 26 are controlled by scanning drivers 32 in turn controlled by microprocessor 22. Optical scanner or scanning reflection densitometer 20 further includes a photocell or optical sensor element 34 for detecting radiation reflected from dosimeter 10. Photocell 34 is operatively connected to microprocessor 22 for feeding thereto an electrical signal identifying the intensity of the reflection from different points on dosimeter 10.

In accordance with the signal from photocell 34, microprocessor 22 acts to determine the optical density of radiation sensitive patch 14 and to decode the parametric information encoded in bar codes 16a and 16b. As discussed in detail hereinafter, microprocessor 22 also functions to compute a quantitative value for a radiation dose from the decoded parameters and the measured optical density of radiation sensitive patch 14, both before and after exposure to radiation.

As further illustrated in FIG. 2, dose reader 18 further includes a display 36 or other communicating component (such as speech synthesis circuitry—not illustrated) which is operatively connected to microprocessor 22 for communicating the computed quantitative radiation dose to an operator. Dose reader 18 additionally includes an electroacoustic transducer or speaker component 38 connected to an output of microprocessor 22 for generating an alert sound in response to a signal from the microprocessor.

A "timer" button 40 and a "zero" button 42 provided on frame 30 are connected to microprocessor 22 for inducing a counting operation and a pre-exposure optical density measurement operation by the microprocessor, respectively. More specifically, timer button 40 is operatively coupled to microprocessor 22 for enabling the post-exposure optical density measurement and computation of the quantitative radiation dose only upon the lapse of a known or predetermined fixed interval after exposure of the layer of radiation sensitive material to radiation. Alternatively, the elapsed time from exposure to read-out can be entered by the operator via a keyboard at the time of dosimeter read-out. In another alternative procedure, the time of radiation exposure is entered into the microprocessor or computer, which determines the elapsed time from exposure to read-out at the time of read-out.

The radiation level to which a subject is exposed is systematically, e.g., linearly, related to the change in optical density of the exposed radiation sensitive patch 14. A predetermined linear mathematical function used by microprocessor 22 in computing the level of radiation exposure is $[\log[I(0)-D]-\log[I(s)-D]-b]/m$ where D is a premeasured background intensity determined for a particular dose reader 18 during production and assembly, m is the slope parameter encoded in bar code 16a or 16b, b is the y-intercept parameter encoded in bar code 16b or 16a, I(0) is a sensed pre-exposure reflection intensity of radiation sensitive patch 14, and I(s) is a sensed post-exposure reflection intensity of patch 14, and $[\log[I(0)-D]-\log[I(s)-D]]$ is a measured/calculated optical density change of patch 14.

As additionally illustrated in FIG. 2, dose reader 18 includes a power button 44 on frame 30. Power button 44 induces the supply of power from a source 46 to various components of the dose reader, including microprocessor 22 and optical scanner or scanning reflection densitometer 20.

Figure 3:
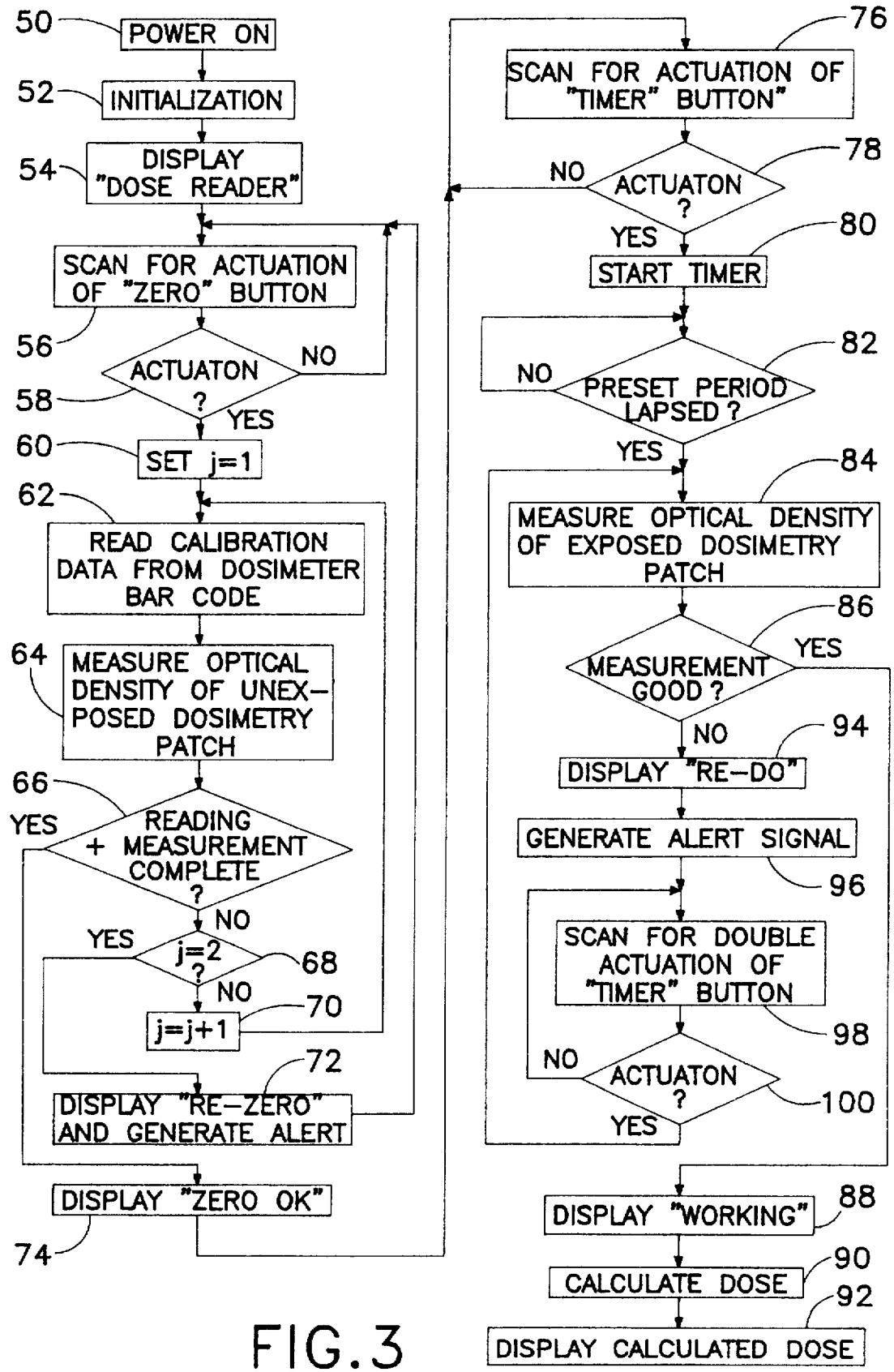
FIG. 3 is a flow chart diagram showing steps in the operation of a microprocessor included in the dose reader of FIG. 2.

FIG. 3 diagrammatically depicts a dosimetry method as controlled by microprocessor 22. Upon a receiving a signal from power button 44 in a step 50, microprocessor 22 undergoes a self-initialization sequence 52 and subsequently energizes display 36, in a step 54, to show the words "Dose Reader." Microprocessor 22 then undertakes a scan 56 to determine whether "zero" button 42 has been actuated. Upon determining at a decision junction 58 that "zero" button 42 has been pressed, microprocessor 22 allots a value of 1 to a temporary parameter j in a step 60 and then cooperates with optical scanner or scanning reflection densitometer 20 in a step 62 to read the calibration data (m, b) for a particular dosimeter 10 from the bar codes 16a and 16b thereon. In addition, microprocessor 22 coacts with optical scanner or scanning reflection densitometer 20 in a step 64 to sense a pre-exposure reflection intensity and calculate a corresponding pre-exposure optical density of radiation sensitive patch 14. Of course, the unexposed densitometer 10 has been inserted into (or slid through) slot 28 prior to (or during) the scanning of the densitometer by optical scanner or scanning reflection densitometer 20.

Upon determining at a decision junction 66 that reading and measurement steps 62 and 64 have not been successfully completed, microprocessor 22 inquires at 68 whether temporary parameter j is equal to 2. If not, parameter j is incremented in a step 70 and microprocessor 22 again undertakes reading and measurement steps 62 and 64. If microprocessor 22 has already made two attempts at reading bar codes 16a and 16b and measuring the optical density of radiation sensitive patch 14, the microprocessor energizes display 36 to show the word "Re-Zero" and generates an audible alert signal via electroacoustic transducer 38 (step 72). Dose reader 18 may also be provided with an additional visual indicator such as a red light (not shown) for alerting a user that dose reader 18 is unable to calibrate or read a dosimeter 10 in slot 28. The dosimeter 10 may be reinserted or another dosimeter card may be tried.

Once microprocessor 22 determines the particular calibration parameters m and b from bar codes 16a and 16b on dosimeter 10, as ascertained at decision junction 66, the microprocessor activates display 36 to display the term "Zero OK" in a step 74 and then scans, in a step 76, for an actuation of timer button 40. An actuation of button 40 means that dosimeter 10 has been removed from slot 28, placed on a subject and irradiated. The user should press button 40 as soon as irradiation has ceased. The user then places the exposed dosimeter 10 back into slot 28.

Upon an actuation of "timer" button 40, detected by microprocessor 22 in an inquiry 78, the microprocessor starts an internal clock running in a step 80. After the passage of a pre-established interval or period of time, monitored by microprocessor 22 in an inquiry 82, the microprocessor coacts with optical scanner or scanning reflection densitometer 20 in a step 84 to measure the optical density of the exposed radiation sensitive patch 14. If the measurement is good, as determined by microprocessor 22 at a decision junction 86, the microprocessor activates display 36 in a step 88, calculates the radiation dose in a step 90 and finally displays the calculated dosage in a step 92. As discussed above, microprocessor 22 computes the level of radiation exposure from the equation or expression [log[I(0)−D]−log[I(s)−D]−b]/m where D is a premeasured background intensity determined for a particular dose reader 18 during production and assembly, m is the slope parameter encoded in bar code 16a or 16b, b is the y-intercept parameter encoded in bar code 16a or 16b. I(0) is a sensed pre-exposure reflection intensity detected in step 64, and I(s) is a sensed post-exposure reflection intensity detected in step 84, while [log|I(0)−D]−log|I(s)−D]] is an optical density change in the layer of radiation sensitive material.

If the measurement of the post-exposure optical density of radiation sensitive patch 14 is unsatisfactory, as determined at decision junction 86, microprocessor 22 energizes display 36 in a step 94 to show the word "Re-do" and energizes electroacoustic transducer 38 in a step 96 to issue an audible alert signal. The microprocessor then waits for a double actuation of timer button 40 (step 98). If the timer button is pressed twice, as determined at 100, microprocessor 22 undertakes immediately another measurement of the optical density of the exposed radiation sensitive patch 14 of the dosimeter 10 in slot 28.

In performing a dosimetry procedure using dosimeter 10 and dose reader 18, the reflectivity of radiation sensitive patch 14 is optically measured prior to exposure thereof to radiation to thereby determine a pre-exposure optical density of patch 14. In addition, bar codes 16a and 16b on dosimeter substrate 12 are scanned to automatically determine the encoded mathematical parameters m and b. Subsequently, after exposure of the dosimeter to radiation and upon lapse of a preset period after the exposure, the post-exposure optical density of radiation sensitive patch 14 is measured optically. Then, in accordance with a predetermined mathematical algorithm incorporating the pre-exposure optical density, the post-exposure optical density, and the decoded or read mathematical parameters m and b, microprocessor 22 automatically computes a quantitative value of the radiation dose to which a subject and the dosimeter 10 were exposed. The computed dose is automatically displayed in virtual real time, i.e., shortly after the irradiation procedure.

The greatest accuracy is obtained by waiting a predetermined period after the termination of an irradiation procedure before measuring the optical density of the exposed patch 14. The radiation sensitive material of patch 14 is well known in the industry.

Preferably, the reading of bar codes 16a and 16b is performed prior to exposure of the dosimeter 10 to radiation. However, the scanning of the parametric codes 16a and 16b and the associated determination of the mathematical parameters m and b may be implemented later, for example, at the time the post-exposure optical density of radiation sensitive patch 14 undertaken.

In an alternative dosimetry method, reflection densitometer 20 (FIG. 2) is a simple densitometer, without the scanning capability provided by scanning drivers 32 and adjustable optics 26. Thus, in dose reader 18, scanning drivers 32 may be omitted. To enable reflection densitometer 20 to sense bar coding 16a and 16b for a determination of mathematical parameters m, b, a user simply slides dosimeter 10 through slot 28, in the same manner that one slides, for example, a credit card through a slot past a magnetic reader. The measurement of the optical density of patch or layer 14 may be made during the same swiping motion of the dosimeter 10. Alternatively, dosimeter 10 may be temporarily left in slot 28 during the measurement of optical density.

It is to be noted that the dosimetry method and dose reader 18 may be modified to enable measurement of the post-exposure optical density of radiation sensitive patch 14 at different times after irradiation has ceased. For example, where the function [log|I(0)−D]−log[I(s)−D]−b]/m is used to calculate the radiation dose from a post-exposure reflection intensity measured a predetermined interval after exposure, the result computed from this expression may be automatically adjusted by microprocessor 22 (FIG. 2) to derive the actual radiation dose when the post-exposure reflection intensity is measured at a different time, i.e., before or after the predetermined post-exposure interval has elapsed. Accordingly, timer button 40 may be used to start a clock internal to microprocessor 22 by which the microprocessor measures the time from the cessation of irradiation to the measurement of optical density. The difference between the measured interval and the preset time period determines a modification amount or adjustment factor to be applied to the calculated radiation dose to derive a final actual radiation dose. To that end, microprocessor 22 is connected to a memory 102 provided in dose reader 18 for storing a table of modification amounts or adjustment factors.

It is advantageous if bar coding 16a, 16b on substrate 12 includes a unique identification of the respective dosimeter 10. This enables, for instance, the utilization of several dosimeters on the same subject during the same irradiation procedure. The pre-exposure optical densities of the radiation sensitive patches 14 of the respective dosimeters 10 are measured in seriatim and stored by microprocessor 22 in memory 102. Later, upon the sliding of a particular exposed dosimeter 10 through slot 28 and the measurement of the post-exposure optical density of that dosimeter, microprocessor 22 accesses memory 102 and retrieves the respective pre-exposure optical density for use in computing the radiation dose experienced by the particular dosimeter 10. Generally, the measured pre-exposure densities are automatically stored by microprocessor 22 in association with the dosimeter identities read from coding 16a, 16b. Addresses in memory 102 for the measured pre-exposure densities may be determined by the dosimeter identities. Alternatively, both the measured pre-exposure densities and the respective dosimeter identities may be stored at associated locations. Of course, when only one dose reader is available for making multiple dose measurements pursuant to this procedure, the above-described table of modification amounts or adjustment factors is necessary.

Figure 4:
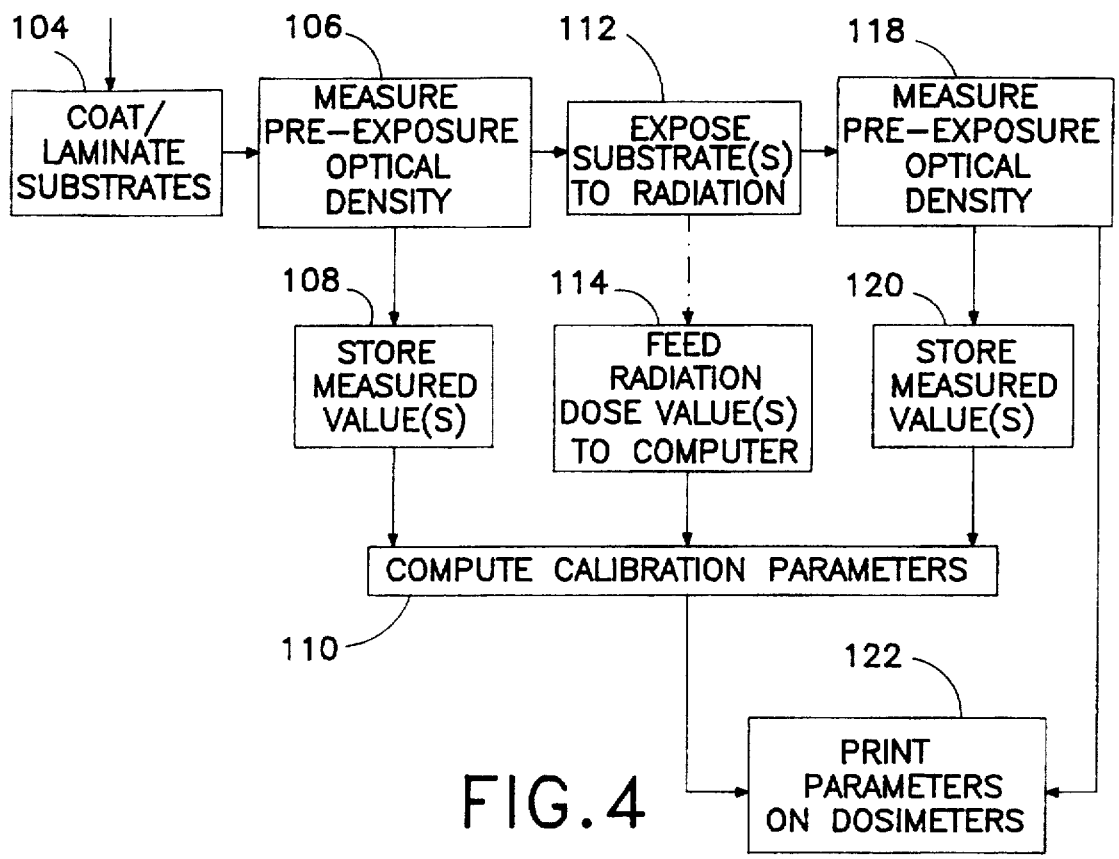
FIG. 4 is a block diagram showing steps in a method for manufacturing an individually calibrated dosimeter, in accordance with the present invention.

As illustrated in FIG. 4, a calibrated dosimeter as described hereinabove with reference to FIG. 1 is manufactured by initially applying a layer of radiation sensitive material to a substrate in a step 104, the radiation sensitive material having an optical density which varies in accordance with a degree of radiation exposure. In a subsequent step 106, a pre-exposure optical density of the layer of radiation sensitive material is optically measured. The measured optical density value is stored in a step 108 for later use in a computation step 110.

After the pre-exposure optical density is measured (step 106), the layer of radiation sensitive material is exposed to a known dose of radiation in step 112. This exposure step may be implemented by transporting a roll of patches to a gamma radiation facility, for example, one operated under the auspices of NIST. The roll of patches is placed perpendicular to the gamma flux and the roll is radiated from both sides. Other refinements may be taken to ensure the uniformity of the irradiation and minimize set-up time. These refinements include providing electron equilibration plates on each side of the roll, irradiating from both sides of the roll, rotating the roll on axis during the irradiation, providing a precise small angle off-set from the perpendicular, and measuring the uniformity of the dose on both sides of the roll with a calibrated dosimeter. Since a roll typically contains a great many patches, the cost involved in calibrating each patch is small. The radiation dose is fed in a step 114 to a computer 116 (FIG. 5) for use in the computation of the calibration parameters in step 110.

After the patches have been exposed to a known radiation dose in step 112, the post-exposure optical densities of the patches are measured in a step 118 and temporarily stored in a step 120. Using the pre-exposure optical density stored in step 108, the post-exposure optical densities stored in step 120, and the known dose of radiation received in step 114, computer 116 (FIG. 5) computes y-intercept b and slope m for each patch in the roll. The computed parameters are applied in encoded form to the respective substrates in step 122. More specifically, the computed y-intercept b and slope m for each patch are printed in bar code form on the respective patches, dosimeters, substrates or holder cards.

Figure 5:
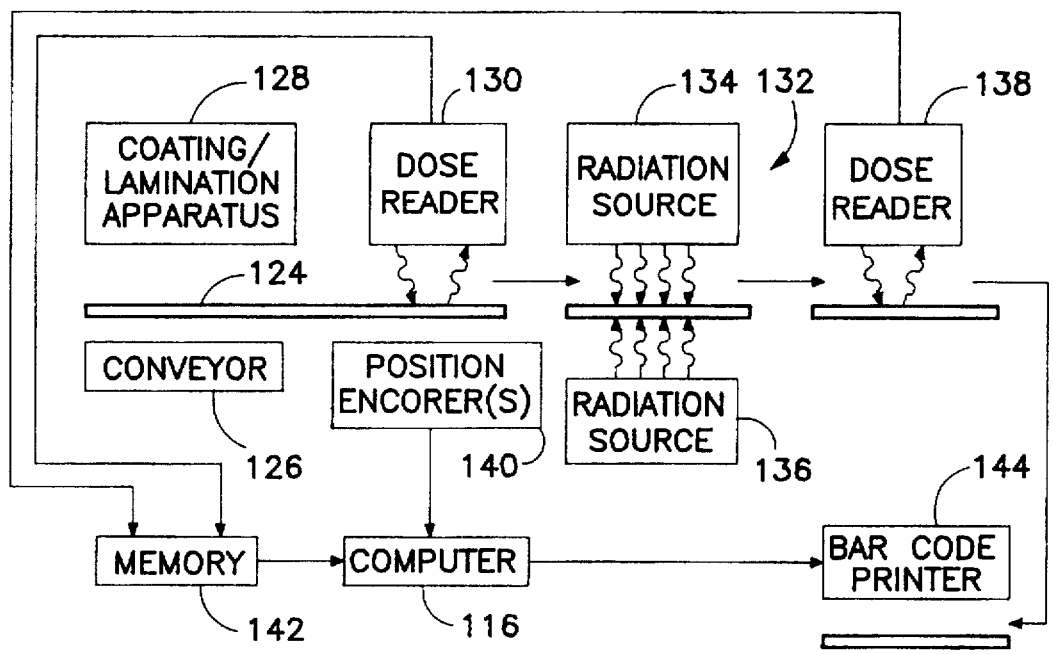
FIG. 5 is a block diagram of an assembly for performing the method illustrated diagrammatically in FIG. 4.

FIG. 5 schematically illustrates a facility for assembly line manufacture of individually calibrated dosimeters 10. A sheet or web 124 is fed by a conveyor 126 to a laminating apparatus 128 wherein a preselected number of coatings of radiation sensitive material such as pentacosadiynoic acid, having predetermined thicknesses, are applied to the sheet 124. Sheet 124 may be wound into a roll (not shown) and transported to a dose reader 130 operationally similar to dose reader 18 described above. Dose reader 130 may include a camera with the same light source and the same optical characteristics as dose reader 18. Dose reader 18 and/or 130 may be a transmission densitometer, which facilitates the use of mirrors to transmit the same measurement beam a plurality of times through a patch, thereby enhancing the sensitivity of the measurement process.

At dose reader 130, the roll of patches or dosimeter substrates is advanced one patch width at a time from an initial starting position into the dose reader 130. Patch sheet 124 is then wound about a take-up roll (not shown) for delivery to a calibration exposure station 132 having one or two high-intensity X-ray units 134 and 136 with ionization type integrating dose rate meters. The integrated dose readout is used to de-activate the X-ray tubes when a preset dose has been reached. The true level of this preset dose level must be calibrated periodically by reference to a secondary standard calibrated by NIST. The correlation between X-rays and gamma rays should be good because the spatial nature of the radiation patterns is similar. Higher accuracy is achievable with the method described above with reference to FIG. 4: pre-exposing the patches in bulk roll form to high energy gamma rays at NIST.

After irradiation at station 132, the film sheet 124 is conveyed to another dose reader 138 (possibly the same as device 130, used to perform the pre-exposure optical density measurements). Dose reader 138 is operated to optically measure the post-exposure optical densities of the individual patches or sensor elements in sheet 124. One or more position encoders 140 cooperate with computer 116 in tracking or identifying the individual patches or sensor elements in sheet 124. Position encoders 140 and computer 116 may assign identification codes such as serial numbers to the individual patches or sensor elements in sheet 124. The identification codes may be used to designate storage cells in a digital memory 142 which is operatively connected at inputs to dose readers 130 and 138 and at an output to computer 116. Memory 142 may also store the radiation dose applied at station 132.

As discussed above, total radiation exposure for a radiation sensitive layer or patch 14 of dosimeter 10 is linearly related to the optical density of the layer or patch 14. Accordingly, computer 116 is programmed to calculate, as the calibration parameters, a slope and a y-intercept. More specifically, computer 116 uses the mathematical function $E_r=[\log[I(0)-D]-\log[I(s)-D]-b]/m$ where $E_r$ is the known radiation dose, D is a premeasured background intensity, m is the slope parameter and b is the y-intercept parameter to be computed, I(0) is the sensed pre-exposure reflection or transmission intensity, and I(s) is the sensed post-exposure reflection or transmission intensity.

As further illustrated in FIG. 5, a bar code printer 144 is connected to computer 116 and disposed downstream of dose reader 138 for providing each dosimeter 10 with a bar code specifying the respective y-intercept and slope parameters of the dosimeter's linear radiation sensitivity function. The dosimeter patches are indexed one patch width at a time through the printer 144, under the control of computer 116 acting in response to signals from encoders 140.

As disclosed above, many, if not all, of the steps in the dosimeter manufacturing process are performed automatically. Specifically, the optical measuring of the pre- and post-exposure optical densities of the layer of radiation sensitive material (steps 106 and 118) and the computing of the calibration parameters (step 110) are performed automatically. In addition, the computed mathematical parameters may be reduced automatically to encoded form (by computer 116) and applied automatically to the dosimeters (step 122). Also, the pre-exposure optical density is automatically stored in electronically encoded form (step 108) and subsequently automatically retrieved to compute the mathematical parameters. Identification codes for the dosimeter patches are automatically generated (by position encoders 140 and computer 116) to distinguish the patches from one another and facilitate correlation of the measured optical densities with the respective patches.

The above described method for individually calibrating the dosimeters 10 is based on the realization that the radiation sensitive layers or patches 14 of the dosimeters 10 have a sufficient density range so that two incremental exposures remain within the linear range of the irradiation reaction, i.e., the change in optical density in response to irradiation. Density change between the time of the calibrating exposure during manufacture and the second exposure during use is not a problem because of the initial "zero" measurement during use.

The principles of dosimeter calibration discussed above can be applied more generally to calibrating a sensor which has an irreversible reaction when subjected to an action, wherein the reaction is progressive and cumulative and related by a known generic mathematical function to the action. The reaction of a sensor is progressive when it varies with the amount of the action to which the sensor is subjected. The reaction is cumulative when it exhibits a total reaction which is a function of the sum of all the actions to which the sensor is subjected. The method described above is generally applicable under these conditions and where the sensor material is not disabled from reacting to further action after being subjected to one or more initial actions. The calibration process described herein serves to determine specific constants of the mathematical function relating the reaction of the sensor to the applied action.

According to this generalized calibration process, the sensor is subjected to a plurality of incremental instances of the action to which the sensor is sensitive, e.g., electromagnetic radiation such as X-rays or gamma rays. Each of the incremental instances of the action have a known magnitude. A cumulative reaction of the sensor to the accumulated amount of the action is measured after each time the sensor is subjected to an instance of the action. And preferably, the condition of the sensor is measured prior to first subjecting the sensor to the action (or energy). In brief, the total number of measurements made to determine the response of the sensor to the cumulative applications of the action is equal to the number of unknown parameters in the mathematical function relating the action to the reaction of the sensor. The unknown parameters of the mathematical function are computed from the known magnitudes of the incremental applications of the action and from the measured cumulative reactions of the sensor.

Figure 6:
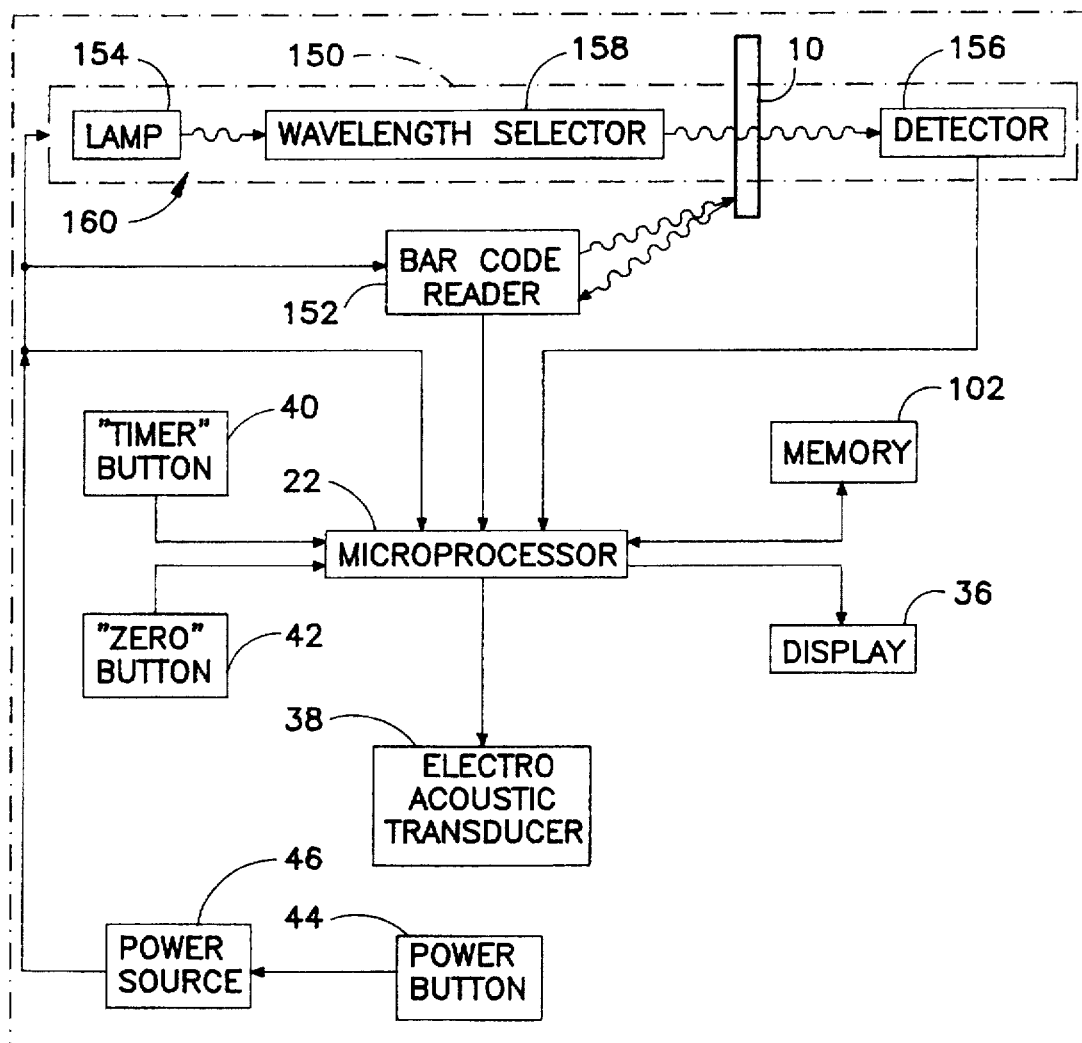
FIG. 6 is a block diagram of a modified dose reader used to determine a radiation dosage received by the dosimeter of FIG. 1. Where

It is to be noted that a preferred embodiment for the dose-reader hardware is a transmission spectrophotometer 150 coupled with a barcode reader 152, as illustrated in FIG. 6. Spectrophotometer 150 enables the measurement of transmission intensity as a function of wavelength. The spectrophotometer is capable of making a succession of measurements of light intensity, each for a slightly different wavelength. In this way, the spectral nature of the absorption band induced by the ionizing radiation can be measured. Use of spectrophotometer 150 for this measurement, instead of densitometer 20 (which typically takes a single measurement for a broad-band of wavelengths), is preferred in order to achieve the (statistical) accuracy that is inherent in making multiple measurements. Also, it will not be necessary to individually calibrate each spectrophotometer, as is necessary when using densitometers to measure colored materials.

The following illustrates the accuracy-enhancing benefit obtained by individual calibration of the dosimeters when measured with multiple-wavelength spectrophotometer 150. During all of these measurements, the intensity of light generated by a lamp 154 of spectrophotometer 150 does not vary; it remains constant throughout.

1) Thirty-six individual dosimeters, constructed of the six-layer radiochromic film laminate described above, were initially measured with the dose-reader hardware to obtain the initial state of each. The measurement was done in the following way:

a) With no dosimeter in place, a spectrum was obtained of lamp 154. This spectrum consists of individual measurements of the light intensity at 14 separate 5-nm wavelength bands, selected by a wavelength selector 158, within a predetermined wavelength region which covers the principal absorption band which the ionizing radiation induces in the selected radiochromic material. Of course, the predetermined wavelength region can be selected to correspond with any absorption band characteristic of any radiochromic material.

b) The first dosimeter was then placed in the instrument and the spectrum was again measured with the dosimeter film 10 disposed between wavelength selector 158 and a light detector 156 of spectrophotometer 150. (Wavelength selector 158 and lamp 154 are parts of a light source 160.)

c) The transmission optical densities (for the first dosimeter) were then calculated for each of the 14 pairs of measurements, according to the formula $\log[J_{lamp}/J_{dosimeter}]$ where $J_{lamp}$ represents the light intensity measured with no dosimeter in place and $J_{dosimeter}$ represents the light intensity measured with the first dosimeter in place.

d) These 14 optical density values (one at each 5-nm wavelength band) were then summed to obtain a number (A1), which is proportional to the "area" under the spectral curve for the first dosimeter.

e) Similarly, optical density "area" values (A2... A36) were obtained for the remaining dosimeters (2 through 36).

2) The 36 dosimeters were then exposed to a known calibration dose (C) of ionizing radiation, causing them to become slightly blue in color.

3) The spectra of the 36 dosimeters were again measured and values were obtained for the calibration dose optical density area values (B1... B36).

4) The calibration factor CAL for each individual dosimeter was then calculated according to:

CAL=(Calibration Dose)/(Measured Area Difference), or

CAL1=$C/(B1-A1)$, CAL2=$C/(B2-A2)$, ... etc.

5) The 36 calibrated dosimeters were then divided into groups of 12 and each group was subjected to radiation, to simulate use of the dosimeter to measure the dose. After measuring the "initial" state of each dosimeter in the group (to obtain optical density area measurements A1, A2, ... etc., as per the first dosimeter above), each group was exposed to a different dose of ionizing radiation. The first twelve dosimeters were exposed to 110 cGy; the second twelve dosimeters were exposed to 165 cGy; and the third twelve dosimeters were exposed to 225 cGy.

6) Each of the 36 dosimeters was then remeasured (to obtain optical density area measurements B1, B2, ... etc., as described in paragraph 3 above, except now the measurement is for the unknown dose, not the "calibration dose"), and the differences between before and after irradiation (B1-A1, B2-A2, ... etc.) were used along with the individual calibration factors (CAL1, CAL2, ... etc.) to calculate the doses according to:

DOSE1=(B1-A1)×CAL1, DOSE2=(B2-A2)×CAL2, ... etc.

The data is presented in the center of Tables I, II, and III set forth below. The errors in these dose calculations are also given: values range from −2.7% to +3.9%.

7) In order to compare these results with a "lot" calibration scenario, the lot average calibration factor (the average of CAL1... CAL36) was determined and this factor was used with the same measured differences between derived optical density area measurements (B1-A1, B2-A2, ... etc.) to calculate the doses. The data is presented on the right side of Tables I, II, and III. The errors in these dose calculations range from −6.8% to +8.3%.

8) For each set of 12 measurements, sample averages and the standard deviation was calculated. The ratio of standard deviation to average (a measure of the spread of the data) was also calculated. It is clear from the data that the "individual calibration" dose calculation is more accurate than the "lot calibration" dose calculation by a factor of more than two:

(3.6/1.3~2.8 for 110 cGy; 2.4/1.1 ~2.2 for 165 cGy; and 3.9/1.1 ~3.5 for 225 cGy).

TABLE I

| Dosimeter ID No. | Measured Difference | Individual Calibration | | | Lot Calibration | | |
|---|---|---|---|---|---|---|---|
| | | Individual Cal Factor | Calculated Dose | % Error | Average Cal Factor | Calculated Dose | % Error |
| 1 | 2.366 | 45.81 | 108.4 | 1.5 | 48.90 | 115.7 | −5.2 |
| 2 | 2.136 | 51.16 | 109.3 | 0.6 | 48.90 | 104.5 | 5.0 |
| 3 | 2.301 | 47.44 | 109.2 | 0.8 | 48.90 | 112.5 | −2.3 |
| 4 | 2.209 | 50.75 | 112.1 | −1.9 | 48.90 | 108.0 | 1.8 |
| 5 | 2.273 | 49.63 | 112.8 | −2.6 | 48.90 | 111.2 | −1.1 |
| 6 | 2.184 | 50.88 | 111.1 | −1.0 | 48.90 | 106.8 | 2.9 |
| 7 | 2.242 | 50.28 | 112.7 | −2.5 | 48.90 | 109.6 | 0.3 |
| 8 | 2.322 | 48.01 | 111.5 | −1.3 | 48.90 | 113.5 | −3.2 |
| 9 | 2.151 | 51.30 | 110.3 | −0.3 | 48.90 | 105.2 | 4.4 |
| 10 | 2.252 | 50.01 | 112.6 | −2.4 | 48.90 | 110.1 | −0.1 |
| 11 | 2.344 | 47.33 | 110.9 | −0.8 | 48.90 | 114.6 | −4.2 |
| 12 | 2.371 | 46.86 | 111.1 | −1.0 | 48.90 | 115.9 | −5.4 |
| 110 cGy Dose | Avg: | | 111.0 | | | 110.6 | |
| | Std: | | 1.5 | | | 4.0 | |
| | Std/Avg (%): | | 1.3 | | | 3.6 | |

TABLE II

| Dosimeter ID No. | Measured Difference | Individual Calibration | | | Lot Calibration | | |
|---|---|---|---|---|---|---|---|
| | | Individual Cal Factor | Calculated Dose | % Error | Average Cal Factor | Calculated Dose | % Error |
| 13 | 3.382 | 48.25 | 163.2 | 1.1 | 48.90 | 165.4 | −0.2 |
| 14 | 3.602 | 46.07 | 165.9 | −0.6 | 48.90 | 176.1 | −6.8 |
| 15 | 3.352 | 49.18 | 164.8 | 0.1 | 48.90 | 163.9 | 0.7 |
| 16 | 3.439 | 48.59 | 167.1 | −1.3 | 48.90 | 168.2 | −1.9 |
| 17 | 3.434 | 49.37 | 169.5 | −2.7 | 48.90 | 167.9 | −1.8 |
| 18 | 3.339 | 49.45 | 165.1 | −0.1 | 48.90 | 163.3 | 1.0 |
| 19 | 3.472 | 48.29 | 167.7 | −1.6 | 48.90 | 169.8 | −2.9 |
| 20 | 3.499 | 47.76 | 167.1 | −1.3 | 48.90 | 171.1 | −3.7 |
| 21 | 3.441 | 47.80 | 164.5 | 0.3 | 48.90 | 168.2 | −2.0 |
| 22 | 3.499 | 47.40 | 165.9 | −0.5 | 48.90 | 171.1 | −3.7 |
| 23 | 3.486 | 47.91 | 167.0 | −1.2 | 48.90 | 170.4 | −3.3 |
| 24 | 3.307 | 50.89 | 168.3 | −2.0 | 48.90 | 161.7 | −2.0 |
| 165 cGy Dose | Avg: | | 166.3 | | | 168.1 | |
| | Std: | | 1.8 | | | 4.0 | |
| | Std/Avg (%): | | 1.1 | | | 2.4 | |

TABLE III

| Dosimeter ID No. | Measured Difference | Individual Calibration | | | Lot Calibration | | |
|---|---|---|---|---|---|---|---|
| | | Individual Cal Factor | Calculated Dose | % Error | Average Cal Factor | Calculated Dose | % Error |
| 25 | 4.219 | 51.83 | 218.7 | 2.8 | 48.90 | 206.3 | 8.3 |
| 26 | 4.534 | 48.99 | 222.1 | 1.3 | 48.90 | 221.7 | 1.5 |
| 27 | 4.493 | 48.11 | 216.2 | 3.9 | 48.90 | 219.7 | 2.4 |
| 28 | 4.562 | 48.56 | 221.5 | 1.5 | 48.90 | 223.1 | 0.8 |
| 29 | 4.461 | 50.67 | 226.1 | −0.5 | 48.90 | 218.2 | 3.0 |
| 30 | 4.254 | 52.05 | 221.4 | 1.6 | 48.90 | 208.0 | 7.5 |

TABLE III-continued

| | | Individual Calibration | | | Lot Calibration | | |
|---|---|---|---|---|---|---|---|
| Dosimeter ID No. | Measured Difference | Individual Cal Factor | Calculated Dose | % Error | Average Cal Factor | Calculated Dose | % Error |
| 31 | 4.340 | 50.87 | 220.8 | 1.9 | 48.90 | 212.2 | 5.7 |
| 32 | 4.713 | 47.13 | 222.1 | 1.3 | 48.90 | 230.5 | -2.4 |
| 33 | 4.466 | 49.49 | 221.0 | 1.8 | 48.90 | 218.4 | 2.9 |
| 34 | 4.612 | 48.07 | 221.7 | 1.5 | 48.90 | 225.5 | -0.2 |
| 35 | 4.686 | 47.54 | 222.8 | 1.0 | 48.90 | 229.1 | -1.8 |
| 36 | 4.782 | 46.50 | 222.4 | 1.2 | 48.90 | 233.9 | -3.9 |
| 225 cGy Dose | Avg: | | 221.4 | | | 220.6 | |
| | Std: | | 2.4 | | | 8.6 | |
| | Std/Avg (%): | | 1.1 | | | 3.9 | |

Although the invention has been described in terms of particular embodiments and applications, one of ordinary skill in the art, in light of this teaching, can generate additional embodiments and modifications without departing from the spirit of or exceeding the scope of the claimed invention. For example, the computing of a radiation dose from a plurality of pre-exposure optical densities and a plurality of post-exposure optical densities as described herein may be viewed as summing the first optical densities to provide a first optical density area measurement $\Sigma\log[I(0)-D]$ and summing the second optical densities to provide a second optical density area measurement $\Sigma\log[I(s)-D]$ and then computing the quantitative radiation dose from these two optical density area measurements in accordance with the relation:

$$[\Sigma\log[I(0)-D]-\Sigma\log[I(s)-D]-b]/m.$$

Alternatively, the computed quantitative radiation dose may be viewed as a summation (average) of individual radiation dose measurements each calculated using a single pre-exposure optical density and an associated post-exposure optical density measured at a common wavelength band of the spectrophotometer, particularly where the y-intercept b has a zero value:

$$\Sigma[\log[I(0)-D]-\log[I(s)-D]-b]/m.$$

Accordingly, it is to be understood that the drawings and descriptions herein are proffered by way of example to facilitate comprehension of the invention and should not be construed to limit the scope thereof.

What is claimed is:

1. A method for determining a level of exposure to radiation, comprising:
   providing a radiation dosimeter including a layer of radiation sensitive material on a substrate, said radiation sensitive material having an optical density which varies in accordance with a degree of radiation exposure, the radiation dosimeter also including an optically readable coding disposed on said substrate, said coding identifying encoded mathematical parameters;
   prior to exposure of said radiation sensitive material to radiation, optically measuring a plurality of first optical densities of said layer of radiation sensitive material at respective different wavelength bands;
   optically scanning said coding to automatically determine said parameters;
   after measuring said first optical densities, exposing said layer of radiation sensitive material to radiation;
   after exposure of said layer of sensitive material to radiation, optically measuring a plurality of second optical densities of said layer of radiation sensitive material at respective ones of said different wavelength bands; and
   automatically computing, from said first optical densities, said second optical densities, and said mathematical parameters and in accordance with a predetermined mathematical function, a quantitative radiation dose to which said layer of radiation sensitive material was exposed, the automatic computing of said quantitative radiation dose including summing said first optical densities and summing said second optical densities.

2. The method defined in claim 1 wherein the optical measuring of a selected optical density from among said first optical densities and said second optical densities includes using a spectrophotometer to subject said layer of radiation sensitive material to light in one of said different wavelength bands.

3. The method defined in claim 2 wherein the optical measuring of said selected optical density includes using said spectrophotometer to measure a first intensity $J_{lamp}$ of light emitted from a source in said one of said different wavelength bands and further using said spectrophotometer to measure a second intensity $J_{dosimeter}$ of light transmitted through said layer of radiation sensitive material from said source in said one of said different wavelength bands, the optical measuring of said selected optical density further including calculating said selected optical density pursuant to the relation $\log[J_{lamp}/J_{dosimeter}]$.

4. The method defined in claim 1, further comprising the step, performed prior to the optical measuring of said first optical densities, of at least temporarily positioning said substrate at a pre-established location in a dose reader instrument.

5. The method defined in claim 4 wherein said substrate is removed from said dose reader instrument and then placed on a subject prior to the exposure of said radiation sensitive material to radiation, said substrate being placed again at least temporarily at said pre-established location after exposure of said radiation sensitive material to radiation and prior to optical measuring of said second optical densities.

6. The method defined in claim 1, further comprising automatically displaying the computed quantitative radiation dose.

7. The method defined in claim 1 wherein the radiation dosimeter is provided with optically readable coding uniquely identifying the dosimeter, further comprising the steps of automatically reading said coding to determine the identity of the dosimeter and automatically storing said first optical densities in electronically encoded form in a memory location associated with the determined identity of the dosimeter.

8. The method defined in claim 1 wherein the step of measuring any given one of said first optical densities includes the step of sensing a pre-exposure intensity of light emanating from said layer of radiation sensitive material in response to light of the respective one of said wavelength bands, the step of measuring a related one of said second optical densities including the step of sensing a post-exposure intensity of light emanating from said layer of radiation sensitive material in response to light of the respective one of said wavelength bands, said predetermined mathematical function being a sum, over all the first optical densities and the related second optical densities, of the relation:

$$[\log[I(0)-D]-\log[I(s)-D]-b]/m$$

where D is a premeasured background intensity, m is a slope parameter included in said mathematical parameters, b is a y-intercept parameter included in said mathematical parameters, I(0) is the pre-exposure intensity at the respective one of said different wavelength bands, I(s) is the post-exposure intensity at the respective one of said different wavelength bands, $\log[I(0)-D]$ is proportional to the respective first optical density, and $\log[I(s)-D]$ is proportional to the respective second optical density.

9. A dose reader instrument comprising:
an optical detector assembly for making a succession of measurements of light intensity in a plurality of different wavelength bands, said optical detector assembly including a light source for generating light at a plurality of different frequencies successively, said optical detector assembly further including an optical sensor for sensing a range of intensities of light emanating from a substrate of radiation sensitive material in response to light from said light source;
a measuring device operatively connected to said optical sensor for determining an optical density of a layer of radiation sensitive material on said substrate;
a decoder operatively connected to said optical sensor for decoding mathematical parameters encoded in an optically readable coding on said substrate;
a computer or microprocessor operatively connected to said measuring device and said decoder for computing, according to a predetermined mathematical function including a measured post-exposure value of optical density and parameters determined from said coding by said decoder, a quantitative radiation dose to which said layer of radiation sensitive material was exposed; and
a communicating component operatively connected to said computer or microprocessor for communicating the computed quantitative radiation dose to an operator.

10. The instrument defined in claim 9, further comprising timing means operatively coupled to said computer or microprocessor for enabling said computer or microprocessor to compute said quantitative radiation dose only upon the lapse of a preset interval after exposure of said layer of radiation sensitive material to radiation.

11. The instrument defined in claim 9, further comprising timing means operatively coupled to said computer or microprocessor for measuring a time interval between exposure of said layer of radiation sensitive material to radiation and an operation of said measuring device to determine said post-exposure value of said optical density, also comprising means operatively connected to said computer or microprocessor for enabling a modification of the computed radiation dose in accordance with a difference between said interval and a preset interval.

12. The instrument defined in claim 11 wherein said means for enabling a modification of the computed radiation dose includes a table of modification values.

13. The instrument defined in claim 9, further comprising (a) additional decoder operatively connected to said optical sensor for decoding a dosimeter identification code on said substrate and (b) a memory operatively connected to said additional decoder and to said measuring device for storing a decoded dosimeter identification code for a selected dosimeter and a measured pre-exposure optical density of said selected dosimeter, said memory being operatively connected to said computer or microprocessor for providing said measured pre-exposure optical density to said computer or microprocessor.

14. The instrument defined in claim 9 wherein said light source includes a wavelength selector.

15. The instrument defined in claim 9 wherein said optical detector assembly is a spectrophotometer.

16. A method for manufacturing a calibrated dosimeter, comprising
providing a substrate;
applying a layer of radiation sensitive material to the substrate, said radiation sensitive material having an optical density which varies in accordance with a degree of radiation exposure;
optically measuring a plurality of pre-exposure optical densities of said layer of radiation sensitive material at respective different wavelength bands;
after measuring said pre-exposure optical densities, exposing said layer of radiation sensitive material to a known dose of radiation;
after exposure of said layer of sensitive material to said known dose of radiation, optically measuring a plurality of post-exposure optical densities of said layer of radiation sensitive material at respective ones of said different wavelength bands;
computing, at least from said pre-exposure optical densities, said post-exposure optical densities, and said known dose of radiation, at least one mathematical parameter defining a predetermined mathematical function, the automatic computing of said quantitative radiation dose including summing said pre-exposure optical densities and summing said post-exposure optical densities, said mathematical parameter being automatically computed from sums of said pre-exposure optical densities and said post exposure optical densities and from said known dose of radiation and in accordance with said predetermined mathematical function; and
applying the computed mathematical parameter in encoded form to said substrate.

17. The method defined in claim 16 wherein the optical measuring of a selected optical density from among said pre-exposure optical densities and said post-exposure optical densities includes using a spectrophotometer to subject said layer of radiation sensitive material to light in one of said different wavelength bands.

18. The method defined in claim 17 wherein the optical measuring of said selected optical density includes using said spectrophotometer to measure a first intensity $J_{lamp}$ of light emitted from a source in said one of said different wavelength bands and further using said spectrophotometer to measure a second intensity $J_{dosimeter}$ of light transmitted through said layer of radiation sensitive material from said source in said one of said different wavelength bands, the optical measuring of said selected optical density further including calculating said selected optical density pursuant to the relation $\log[J_{lamp}/J_{dosimeter}]$.

19. The method defined in claim 16 wherein the optical measuring of any one of said pre-exposure optical densities and said post-exposure optical densities is performed automatically.

20. The method defined in claim 16, further comprising automatically reducing the computed mathematical parameters to encoded form, the mathematical parameters being applied automatically to said substrate.

21. The method defined in claim 16 wherein the mathematical parameters are encoded in optically readable form.

22. The method defined in claim 16, further comprising a step of providing said substrate with optically readable coding uniquely identifying the respective dosimeter.

* * * * *